United States Patent
Yu

(10) Patent No.: US 11,376,085 B2
(45) Date of Patent: *Jul. 5, 2022

(54) REMOTE CATHETER MANIPULATOR

(71) Applicant: Auris Health, Inc., Redwood City, CA (US)

(72) Inventor: Alan Yu, Redwood City, CA (US)

(73) Assignee: Auris Health, Inc., Redwood City, CA (US)

( * ) Notice: Subject to any disclaimer, the term of this patent is extended or adjusted under 35 U.S.C. 154(b) by 353 days.

This patent is subject to a terminal disclaimer.

(21) Appl. No.: 16/740,973

(22) Filed: Jan. 13, 2020

(65) Prior Publication Data

US 2020/0155245 A1 May 21, 2020

Related U.S. Application Data

(63) Continuation of application No. 15/390,355, filed on Dec. 23, 2016, now Pat. No. 10,543,047, which is a continuation of application No. 13/839,967, filed on Mar. 15, 2013, now abandoned.

(51) Int. Cl.
*A61B 34/30* (2016.01)
*A61M 25/01* (2006.01)
*A61B 17/00* (2006.01)

(52) U.S. Cl.
CPC ......... *A61B 34/30* (2016.02); *A61M 25/0113* (2013.01); *A61B 2017/00292* (2013.01); *A61B 2034/301* (2016.02); *A61B 2034/304* (2016.02)

(58) Field of Classification Search
CPC ......... A61B 34/30; A61B 2017/00292; A61M 25/0113; A61M 25/0116
See application file for complete search history.

(56) References Cited

U.S. PATENT DOCUMENTS

| | | | |
|---|---|---|---|
| 2,556,601 A | 6/1951 | Schofield |
| 2,566,183 A | 8/1951 | Forss |
| 2,623,175 A | 12/1952 | Finke |
| 2,730,699 A | 1/1956 | Gratian |
| 2,884,808 A | 5/1959 | Mueller |

(Continued)

FOREIGN PATENT DOCUMENTS

| | | |
|---|---|---|
| CN | 101161426 | 4/2008 |
| CN | 103037799 | 4/2011 |

(Continued)

OTHER PUBLICATIONS

Mayo Clinic, Robotic Surgery, https://www.mayoclinic.org/tests-procedures/robotic-surgery/about/pac-20394974?p=1, downloaded from the internet on Jul. 12, 2018, 2 pp.

(Continued)

*Primary Examiner* — Tuan V Nguyen
(74) *Attorney, Agent, or Firm* — Frost Brown Todd LLC

(57) ABSTRACT

A robotic instrument driver for elongate members includes a first elongate member, and at least one manipulator mechanism configured to manipulate the first elongate member, and at least one articulating drive configured to articulate the first elongate member, positionable on a bed and beside a patient access site. The manipulator and articulating drive are positioned relative to each other a distance less than the insertable length of the first elongate member, stationary in position.

20 Claims, 7 Drawing Sheets

(56) References Cited

U.S. PATENT DOCUMENTS

| | | |
|---|---|---|
| 3,294,183 A | 12/1966 | Riley et al. |
| 3,472,083 A | 10/1969 | Schnepel |
| 3,513,724 A | 5/1970 | Box |
| 3,595,074 A | 7/1971 | Johnson |
| 3,734,207 A | 5/1973 | Fishbein |
| 3,739,923 A | 6/1973 | Totsuka |
| 3,784,031 A | 1/1974 | Nitu |
| 3,790,002 A | 2/1974 | Guilbaud et al. |
| 3,921,536 A | 11/1975 | Savage |
| 3,926,386 A | 12/1975 | Stahmann |
| 4,141,245 A | 2/1979 | Brandstetter |
| 4,241,884 A | 12/1980 | Lynch |
| 4,243,034 A | 1/1981 | Brandt |
| 4,351,493 A | 9/1982 | Sonnek |
| 4,357,843 A | 11/1982 | Peck et al. |
| 4,384,493 A | 5/1983 | Grunbaum |
| 4,507,026 A | 3/1985 | Lund |
| 4,530,471 A | 7/1985 | Inoue |
| 4,555,960 A | 12/1985 | King |
| 4,688,555 A | 8/1987 | Wardle |
| 4,745,908 A | 5/1988 | Wardle |
| 4,784,150 A | 11/1988 | Voorhies et al. |
| 4,857,058 A | 8/1989 | Payton |
| 4,907,168 A | 3/1990 | Boggs |
| 4,945,790 A | 8/1990 | Golden |
| 5,207,128 A | 5/1993 | Albright |
| 5,234,428 A | 8/1993 | Kaufman |
| 5,256,150 A | 10/1993 | Qulachon et al. |
| 5,277,085 A | 1/1994 | Tanimura et al. |
| 5,350,101 A | 9/1994 | Godlewski |
| 5,398,691 A | 3/1995 | Martin et al. |
| 5,408,409 A | 4/1995 | Glassman et al. |
| 5,426,687 A | 6/1995 | Goodall et al. |
| 5,507,725 A | 4/1996 | Savage et al. |
| 5,524,180 A | 6/1996 | Wang et al. |
| 5,559,294 A | 9/1996 | Hoium et al. |
| 5,631,973 A | 5/1997 | Green |
| 5,709,661 A | 1/1998 | Van Egmond |
| 5,713,946 A | 2/1998 | Ben-Haim |
| 5,749,362 A | 5/1998 | Funda et al. |
| 5,767,840 A | 6/1998 | Selker |
| 5,779,623 A | 7/1998 | Bonnell |
| 5,792,135 A | 8/1998 | Madhani et al. |
| 5,797,900 A | 8/1998 | Madhani |
| 5,842,390 A | 12/1998 | Bouligny |
| 5,855,583 A | 1/1999 | Wang et al. |
| 5,859,934 A | 1/1999 | Green |
| 5,876,325 A | 3/1999 | Mizuno et al. |
| 5,921,968 A | 7/1999 | Lampropoulos et al. |
| 5,951,475 A | 9/1999 | Gueziec et al. |
| 5,967,934 A | 10/1999 | Ishida et al. |
| 6,077,219 A | 6/2000 | Viebach |
| 6,084,371 A | 7/2000 | Kress et al. |
| 6,154,000 A | 11/2000 | Rastegar et al. |
| 6,171,234 B1 | 1/2001 | White et al. |
| 6,185,478 B1 | 2/2001 | Koakutsu et al. |
| 6,226,543 B1 | 5/2001 | Gilboa et al. |
| 6,259,806 B1 | 7/2001 | Green |
| 6,272,371 B1 | 8/2001 | Shlomo |
| 6,289,579 B1 | 9/2001 | Viza et al. |
| 6,394,998 B1 | 5/2002 | Wallace et al. |
| 6,401,572 B1 | 6/2002 | Provost |
| 6,424,885 B1 | 7/2002 | Niemeyer et al. |
| 6,436,107 B1 | 8/2002 | Wang et al. |
| 6,487,940 B2 | 12/2002 | Hart et al. |
| 6,491,701 B2 | 12/2002 | Tierney et al. |
| 6,550,128 B1 | 4/2003 | Lorenz |
| 6,695,818 B2 | 2/2004 | Wollschlager |
| 6,726,675 B1 | 4/2004 | Beyar |
| 6,786,896 B1 | 9/2004 | Madhani et al. |
| 6,827,712 B2 | 12/2004 | Tovey et al. |
| 7,044,936 B2 | 5/2006 | Harding |
| 7,155,315 B2 | 12/2006 | Niemeyer et al. |
| 7,172,580 B2 | 2/2007 | Hruska et al. |
| 7,276,044 B2 | 10/2007 | Ferry et al. |
| 7,615,042 B2 | 11/2009 | Beyar et al. |
| 7,635,342 B2 | 12/2009 | Ferry et al. |
| 7,766,856 B2 | 8/2010 | Ferry et al. |
| 7,789,874 B2 | 9/2010 | Yu et al. |
| 7,938,809 B2 | 5/2011 | Lampropoulos et al. |
| 7,972,298 B2 | 7/2011 | Wallace et al. |
| 7,974,674 B2 | 7/2011 | Hauck et al. |
| 7,998,020 B2 | 8/2011 | Kidd et al. |
| 8,052,636 B2 | 11/2011 | Moll et al. |
| 8,146,874 B2 | 4/2012 | Yu |
| 8,157,308 B2 | 4/2012 | Pedersen |
| 8,182,415 B2 | 5/2012 | Larkin et al. |
| 8,277,417 B2 | 10/2012 | Fedinec et al. |
| 8,291,791 B2 | 10/2012 | Light et al. |
| 8,414,505 B1 | 4/2013 | Weitzner |
| 8,425,465 B2 | 4/2013 | Nagano |
| 8,671,817 B1 | 3/2014 | Bogusky |
| 8,720,448 B2 | 5/2014 | Reis et al. |
| 8,746,252 B2 | 6/2014 | McGrogan et al. |
| 8,870,815 B2 | 10/2014 | Bhat et al. |
| 8,961,533 B2 | 2/2015 | Startler et al. |
| 8,968,333 B2 | 3/2015 | Yu et al. |
| 8,992,542 B2 | 3/2015 | Hagag et al. |
| 9,023,068 B2 | 5/2015 | Viola |
| 9,173,713 B2 | 11/2015 | Hart et al. |
| 9,204,933 B2 | 12/2015 | Reis et al. |
| 9,259,281 B2 | 2/2016 | Griffiths et al. |
| 9,314,306 B2 | 4/2016 | Yu |
| 9,326,822 B2 | 5/2016 | Lewis et al. |
| 9,408,669 B2 | 8/2016 | Kokish et al. |
| 9,446,177 B2 | 9/2016 | Millman et al. |
| 9,452,018 B2 | 9/2016 | Yu |
| 9,457,168 B2 | 10/2016 | Moll et al. |
| 9,498,601 B2 | 11/2016 | Tanner et al. |
| 9,504,604 B2 | 11/2016 | Alvarez |
| 9,561,083 B2 | 2/2017 | Yu et al. |
| 9,566,201 B2 | 2/2017 | Yu |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,659 B2 | 3/2018 | Chopra |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 9,993,614 B2 | 6/2018 | Pacheco |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,136,959 B2 | 11/2018 | Mintz et al. |
| 10,143,360 B2 | 12/2018 | Roelle et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,213,264 B2 | 2/2019 | Tanner et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,258,285 B2 | 4/2019 | Hauck |
| 10,285,574 B2 | 5/2019 | Landey et al. |
| 10,299,870 B2 | 5/2019 | Connolly et al. |
| 10,314,463 B2 | 6/2019 | Agrawal et al. |

(56) References Cited

U.S. PATENT DOCUMENTS

| | | |
|---|---|---|
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,454,347 B2 | 10/2019 | Covington et al. |
| 10,464,209 B2 | 11/2019 | Ho et al. |
| 10,470,830 B2 | 11/2019 | Hill |
| 10,478,595 B2 | 11/2019 | Kokish |
| 10,482,599 B2 | 11/2019 | Mintz et al. |
| 10,493,239 B2 | 12/2019 | Hart et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,524,867 B2 | 1/2020 | Kokish et al. |
| 10,539,478 B2 | 1/2020 | Lin |
| 10,543,047 B2 | 1/2020 | Yu |
| 10,543,048 B2 | 1/2020 | Noonan et al. |
| 10,555,778 B2 | 2/2020 | Ummalaneni et al. |
| 10,556,092 B2 | 2/2020 | Yu et al. |
| 10,569,052 B2 | 2/2020 | Kokish et al. |
| 10,765,487 B2 | 9/2020 | Ho |
| 2001/0042643 A1 | 11/2001 | Krueger et al. |
| 2002/0045905 A1 | 4/2002 | Gerbi et al. |
| 2002/0098938 A1 | 7/2002 | Milbourne et al. |
| 2002/0100254 A1 | 8/2002 | Dharssi |
| 2002/0107573 A1 | 8/2002 | Steinberg |
| 2002/0117017 A1 | 8/2002 | Bernhardt et al. |
| 2002/0161355 A1 | 10/2002 | Wollschlager |
| 2002/0161426 A1 | 10/2002 | Lancea |
| 2002/0177789 A1 | 11/2002 | Ferry et al. |
| 2003/0056561 A1 | 3/2003 | Butscher et al. |
| 2003/0167623 A1 | 9/2003 | Lorenz |
| 2003/0212308 A1 | 11/2003 | Bendall |
| 2004/0015053 A1 | 1/2004 | Bieger |
| 2004/0152972 A1 | 8/2004 | Hunter |
| 2004/0243147 A1 | 12/2004 | Lipow |
| 2004/0254566 A1 | 12/2004 | Plicchi |
| 2005/0004579 A1 | 1/2005 | Schneider et al. |
| 2005/0177026 A1 | 8/2005 | Hoeg et al. |
| 2005/0183532 A1 | 8/2005 | Najaf et al. |
| 2005/0222554 A1 | 10/2005 | Wallace et al. |
| 2006/0025676 A1 | 2/2006 | Viswanathan et al. |
| 2006/0041245 A1 | 2/2006 | Ferry |
| 2006/0111692 A1 | 5/2006 | Hlavka et al. |
| 2006/0146010 A1 | 7/2006 | Schneider |
| 2006/0201688 A1 | 9/2006 | Jenner et al. |
| 2006/0229587 A1 | 10/2006 | Beyar et al. |
| 2006/0237205 A1 | 10/2006 | Sia et al. |
| 2007/0000498 A1 | 1/2007 | Glynn et al. |
| 2007/0013336 A1 | 1/2007 | Nowlin et al. |
| 2007/0060879 A1 | 3/2007 | Weilzner et al. |
| 2007/0100201 A1 | 5/2007 | Komiya et al. |
| 2007/0100254 A1 | 5/2007 | Murakami |
| 2007/0112355 A1 | 5/2007 | Salahieh |
| 2007/0119274 A1 | 5/2007 | Devengenzo et al. |
| 2007/0149946 A1 | 6/2007 | Viswanathan |
| 2007/0185485 A1 | 8/2007 | Hauck et al. |
| 2007/0185486 A1 | 8/2007 | Hauck et al. |
| 2007/0191177 A1 | 8/2007 | Nagai et al. |
| 2007/0239028 A1 | 10/2007 | Houser |
| 2007/0245175 A1 | 10/2007 | Zheng et al. |
| 2007/0299427 A1 | 12/2007 | Yeung et al. |
| 2008/0039255 A1 | 2/2008 | Jinno et al. |
| 2008/0046122 A1 | 2/2008 | Manzo et al. |
| 2008/0065103 A1 | 3/2008 | Cooper et al. |
| 2008/0147011 A1 | 6/2008 | Urmey |
| 2008/0177285 A1 | 7/2008 | Brock et al. |
| 2008/0214925 A1 | 9/2008 | Wilson et al. |
| 2008/0243064 A1 | 10/2008 | Stabler et al. |
| 2008/0245946 A1 | 10/2008 | Yu |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0287963 A1 | 11/2008 | Rogers et al. |
| 2008/0302200 A1 | 12/2008 | Tobey |
| 2009/0005768 A1 | 1/2009 | Sharareh |
| 2009/0082722 A1 | 3/2009 | Munger et al. |
| 2009/0098971 A1 | 4/2009 | Ho et al. |
| 2009/0105645 A1 | 4/2009 | Kidd et al. |
| 2009/0163948 A1 | 6/2009 | Sunaoshi |
| 2009/0171371 A1 | 7/2009 | Nixon |
| 2009/0247944 A1 | 10/2009 | Kirschenman et al. |
| 2009/0248039 A1 | 10/2009 | Cooper et al. |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0130923 A1 | 5/2010 | Cleary et al. |
| 2010/0130987 A1 | 5/2010 | Wenderow et al. |
| 2010/0175701 A1 | 7/2010 | Reis et al. |
| 2010/0187740 A1 | 7/2010 | Orgeron |
| 2010/0204646 A1 | 8/2010 | Plicchi et al. |
| 2010/0210923 A1 | 8/2010 | Li et al. |
| 2010/0248177 A1 | 9/2010 | Mangelberger et al. |
| 2010/0249506 A1 | 9/2010 | Prisco et al. |
| 2010/0274078 A1 | 10/2010 | Kim et al. |
| 2010/0332033 A1 | 12/2010 | Diolaiti |
| 2011/0015484 A1 | 1/2011 | Alvarez et al. |
| 2011/0015648 A1 | 1/2011 | Alvarez et al. |
| 2011/0015650 A1 | 1/2011 | Choi et al. |
| 2011/0028991 A1 | 2/2011 | Ikeda et al. |
| 2011/0130718 A1 | 6/2011 | Kidd et al. |
| 2011/0147030 A1 | 6/2011 | Blum et al. |
| 2011/0152880 A1 | 6/2011 | Alvarez et al. |
| 2011/0238083 A1 | 9/2011 | Moll et al. |
| 2011/0261183 A1 | 10/2011 | Ma et al. |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2012/0071821 A1 | 3/2012 | Yu |
| 2012/0071894 A1 | 3/2012 | Tanner et al. |
| 2012/0071895 A1 | 3/2012 | Stabler et al. |
| 2012/0132018 A1 | 5/2012 | Tang |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0232476 A1* | 9/2012 | Bhat .................. A61B 34/30 226/176 |
| 2012/0239012 A1 | 9/2012 | Laurent et al. |
| 2012/0277730 A1 | 11/2012 | Salahieh |
| 2012/0283747 A1 | 11/2012 | Popovic |
| 2013/0018400 A1 | 1/2013 | Milton et al. |
| 2013/0066335 A1 | 3/2013 | Barwinkel |
| 2013/0144116 A1 | 6/2013 | Cooper |
| 2013/0231678 A1 | 9/2013 | Wenderow |
| 2013/0304084 A1 | 11/2013 | Beira et al. |
| 2013/0317519 A1 | 11/2013 | Romo et al. |
| 2013/0345519 A1 | 12/2013 | Piskun et al. |
| 2014/0000411 A1 | 1/2014 | Shelton, IV et al. |
| 2014/0066944 A1 | 3/2014 | Taylor et al. |
| 2014/0069437 A1 | 3/2014 | Reis et al. |
| 2014/0142591 A1 | 5/2014 | Alvarez et al. |
| 2014/0166023 A1 | 6/2014 | Kishi |
| 2014/0171778 A1 | 6/2014 | Tsusaka |
| 2014/0180063 A1 | 6/2014 | Zhao |
| 2014/0222019 A1 | 8/2014 | Brudnick |
| 2014/0243849 A1 | 8/2014 | Saglam et al. |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |
| 2014/0276647 A1 | 9/2014 | Yu |
| 2014/0276935 A1 | 9/2014 | Yu |
| 2014/0276936 A1 | 9/2014 | Kokish et al. |
| 2014/0277334 A1 | 9/2014 | Yu et al. |
| 2014/0357984 A1 | 12/2014 | Wallace et al. |
| 2014/0364870 A1 | 12/2014 | Alvarez et al. |
| 2014/0375784 A1 | 12/2014 | Massetti |
| 2015/0012134 A1 | 1/2015 | Robinson |
| 2015/0090063 A1 | 4/2015 | Lantermann et al. |

(56) References Cited

U.S. PATENT DOCUMENTS

| | | |
|---|---|---|
| 2015/0133858 A1 | 5/2015 | Julian et al. |
| 2015/0133963 A1 | 5/2015 | Barbagli |
| 2015/0142013 A1 | 5/2015 | Tanner et al. |
| 2015/0144514 A1 | 5/2015 | Brennan et al. |
| 2015/0148600 A1 | 5/2015 | Ashinuma et al. |
| 2015/0150635 A1 | 6/2015 | Kilroy |
| 2015/0182250 A1 | 7/2015 | Conlon et al. |
| 2015/0231364 A1 | 8/2015 | Blanchard |
| 2015/0374445 A1 | 12/2015 | Gombert et al. |
| 2016/0000512 A1 | 1/2016 | Gombert et al. |
| 2016/0001038 A1 | 1/2016 | Romo et al. |
| 2016/0100896 A1 | 4/2016 | Yu |
| 2016/0157945 A1 | 6/2016 | Madhani |
| 2016/0166234 A1 | 6/2016 | Zhang |
| 2016/0192860 A1 | 7/2016 | Allenby |
| 2016/0206389 A1 | 7/2016 | Miller |
| 2016/0213435 A1 | 7/2016 | Hourtash |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2017/0007337 A1 | 1/2017 | Dan |
| 2017/0007343 A1 | 1/2017 | Yu |
| 2017/0119481 A1 | 5/2017 | Romo et al. |
| 2017/0151028 A1 | 6/2017 | Ogawa et al. |
| 2017/0165011 A1 | 6/2017 | Bovay et al. |
| 2017/0202627 A1 | 7/2017 | Sramek et al. |
| 2017/0209073 A1 | 7/2017 | Sramek et al. |
| 2017/0252540 A1 | 9/2017 | Weitzner et al. |
| 2017/0258534 A1 | 9/2017 | Hourtash |
| 2017/0281049 A1 | 10/2017 | Yamamoto |
| 2017/0290631 A1 | 10/2017 | Lee et al. |
| 2017/0325932 A1 | 11/2017 | Hoelzle |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0042464 A1 | 2/2018 | Arai |
| 2018/0042686 A1 | 2/2018 | Peine |
| 2018/0049792 A1 | 2/2018 | Eckert |
| 2018/0056044 A1 | 3/2018 | Choi et al. |
| 2018/0194820 A1 | 4/2018 | Troy et al. |
| 2018/0116735 A1 | 5/2018 | Tierney et al. |
| 2018/0206927 A1 | 7/2018 | Prisco et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0243048 A1 | 8/2018 | Shan |
| 2018/0250083 A1 | 9/2018 | Schuh et al. |
| 2018/0271616 A1 | 9/2018 | Schuh et al. |
| 2018/0279852 A1 | 10/2018 | Rafii-Tar et al. |
| 2018/0280660 A1 | 10/2018 | Landey et al. |
| 2018/0289431 A1 | 10/2018 | Draper et al. |
| 2018/0296299 A1 | 10/2018 | Iceman |
| 2018/0303566 A1 | 10/2018 | Soundararajan |
| 2018/0325499 A1 | 11/2018 | Landey et al. |
| 2018/0326181 A1 | 11/2018 | Kokish et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0110839 A1 | 4/2019 | Rafii-Tar et al. |
| 2019/0151148 A1 | 4/2019 | Alvarez et al. |
| 2019/0142537 A1 | 5/2019 | Covington et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223967 A1 | 7/2019 | Abbott |
| 2019/0223974 A1 | 7/2019 | Romo |
| 2019/0228525 A1 | 7/2019 | Mintz et al. |
| 2019/0231458 A1 | 8/2019 | DiMaio |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0008874 A1 | 1/2020 | Barbagli et al. |
| 2020/0022767 A1 | 1/2020 | Hill |
| 2020/0039086 A1 | 2/2020 | Meyer |
| 2020/0046434 A1 | 2/2020 | Graetzel |
| 2020/0054405 A1 | 2/2020 | Schuh |
| 2020/0054408 A1 | 2/2020 | Schuh et al. |
| 2020/0060516 A1 | 2/2020 | Baez |
| 2020/0086087 A1 | 3/2020 | Hart et al. |
| 2020/0091799 A1 | 3/2020 | Covington et al. |
| 2020/0093549 A1 | 3/2020 | Chin |
| 2020/0093554 A1 | 3/2020 | Schuh |
| 2020/0100845 A1 | 4/2020 | Julian |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0129252 A1 | 4/2020 | Kokish |
| 2020/0146769 A1 | 5/2020 | Eyre |
| 2020/0155801 A1 | 5/2020 | Kokish |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0230360 A1 | 7/2020 | Yu |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |

FOREIGN PATENT DOCUMENTS

| | | |
|---|---|---|
| CN | 201884596 U | 6/2011 |
| CN | 102316817 | 1/2012 |
| CN | 102327118 | 1/2012 |
| CN | 102458295 | 5/2012 |
| CN | 102665590 | 9/2012 |
| CN | 102834043 | 12/2012 |
| CN | 102973317 | 3/2013 |
| CN | 102015759 | 4/2013 |
| CN | 103735313 | 4/2014 |
| CN | 105147393 | 12/2015 |
| CN | 105559850 | 5/2016 |
| CN | 105559886 | 5/2016 |
| DE | 19649082 | 1/1998 |
| DE | 102004020465 | 9/2005 |
| EP | 1 442 720 | 8/2004 |
| EP | 2 567 670 | 3/2013 |
| EP | 3 025 630 | 6/2016 |
| JP | 07-136173 | 5/1995 |
| JP | 2009-139187 | 6/2009 |
| JP | 2010-046384 | 3/2010 |
| WO | WO 02/74178 | 9/2002 |
| WO | WO 03/086190 | 10/2003 |
| WO | WO 07/146987 | 12/2007 |
| WO | WO 09/092059 | 7/2009 |

(56) References Cited

FOREIGN PATENT DOCUMENTS

| WO | WO 11/005335 | 1/2011 |
| WO | WO 12/037506 | 3/2012 |
| WO | WO 13/179600 | 12/2013 |
| WO | WO 15/127231 | 8/2015 |
| WO | WO 17/059412 | 4/2017 |
| WO | WO 17/151993 | 9/2017 |

OTHER PUBLICATIONS

European Search Report for European Patent Application No. 14160078.3 dated Feb. 11, 2015. (6 pages).

* cited by examiner

REMOTE CATHETER MANIPULATOR

CROSS-REFERENCE TO RELATED APPLICATION

This application is a continuation of U.S. patent application Ser. No. 15/390,355, filed Dec. 23, 2016 and entitled "REMOTE CATHETER MANIPULATOR," which is a continuation of U.S. patent application Ser. No. 13/839,967, filed Mar. 15, 2013 and entitled "VASCULAR REMOTE CATHETER MANIPULATOR." The foregoing applications are hereby incorporated by reference in their entireties for all purposes.

BACKGROUND

Robotic interventional systems and devices are well suited for performing minimally invasive medical procedures as opposed to conventional techniques wherein the patient's body cavity is open to permit the surgeon's hands access to internal organs. Advances in technology have led to significant changes in the field of medical surgery such that less invasive surgical procedures, in particular, minimally invasive surgery (MIS), are increasingly popular.

MIS is generally defined as surgery that is performed by entering the body through the skin, a body cavity, or an anatomical opening utilizing small incisions rather than large, open incisions in the body. With MIS, it is possible to achieve less operative trauma for the patient, reduced hospitalization time, less pain and scarring, reduced incidence of complications related to surgical trauma, lower costs, and a speedier recovery.

MIS devices and techniques have advanced to the point where an elongated catheter instrument is controllable by selectively operating tensioning control elements within the catheter instrument. In one example, a remote catheter manipulator (RCM) or robotic instrument driver utilizes four opposing directional control elements which extend to the distal end of the catheter. When selectively placed in and out of tension, the opposing directional control elements may cause the distal end to steerably maneuver within the patient. Control motors are coupled to each of the directional control elements so that they may be individually controlled and the steering effectuated via the operation of the motors in unison.

At least two types of catheters may be employed for surgical procedures. One type includes an electrophysiology (EP) catheter that only requires a navigating distance of 15 cm or less. EP catheters also may be relatively thick and stiff and thus, due their short navigating length and high stiffness, EP catheters typically do not suffer from a tendency to buckle during use.

In comparison to EP procedures, vascular procedures include a greater amount of catheter insertion length, a greater number of catheter articulation degrees of freedom (DOFs), and a mechanism for manipulation of a guide wire. For that reason, known bedside systems provides mounting for splayer actuation hardware configured to provide the catheter insertion lengths, mounting which accounts for an increase in splayer size due to added DOFs, and mounting for a guide wire manipulator. Thus, vascular catheters typically include a relatively long stroke, such as one meter or more. Relative to EP catheters, vascular catheters are typically smaller, thinner and more flexible, and therefore have a greater tendency to buckle than EP catheters. As such, it is typically desirable to feed vascular catheters into the patient with minimal bending to reduce the tendency to buckle. Known vascular robotic catheter systems are therefore typically suspended over the patient that is lying prone on a bed.

A vascular catheter (elongate member) catheter system typically includes elongate members that include an outer catheter (sheath), an inner catheter (leader), and a guidewire. Each is separately controllable and therefore they can telescope with respect to one another. For instance, a sheath carriage controls operation of the sheath and is moveable about a generally axial motion along the patient, and a leader carriage controls operation of the guidewire and is likewise moveable about the generally axial direction of the patient. Typically, the leader carriage and the sheath carriage are positioned on a remote catheter manipulator (RCM), which is supported by a setup joint (SUJ). Because the sheath carriage and leader carriage are traditionally aligned along the insertion axis, this configuration results in the RCM taking up significant space and the RCM being restricted to a specific orientation and alignment based on the insertion location. The SUJ is typically positioned on a rail that is itself mounted to the bed, below which the patient is positioned.

The RCM typically carries the weight of both carriages as well as the other hardware that are used to operate the system. And, to provide a full stroke, the SUJ is passed through the full range of motion which, as stated, can exceed one meter. To do so, typically the SUJ is moved or rotated with respect to the rail and the rail is stationary. For this reason, a bedside system is typically included that provides mounting for splayer actuation hardware configured to provide catheter insertion lengths, and mounting for a guide wire manipulator. Because this hardware is supported by the SUJ, the system can not only be cumbersome to work with, but it can interfere with other system operation (such as the C-arm and monitors), as well as provide significant weight that is carried by the bed.

However, in some clinical situations, it is difficult, if not impossible to orient the RCM such that it is aligned along the insertion axis. For instance, in some MIS procedures an imaging device may be required in addition to the RCM. In order for the imaging device to scan the entire body, the RCM should be oriented so that it is not obstructing the imaging devices ability to capture the entire body. For example, if the insertion location is at the patient's thigh and catheter is directed towards the patient's heart, the current RCM configuration would require the RCM to be located at the base of the patient's bed below their feet. The likelihood of the catheter buckling between the RCM and the insertion location also increases as the distance between the RCM and the insertion location increases and often requires more than one person to assist in operation of the RCM, especially during tool exchanges.

As such, there is a need for an improved catheter system that can handle functional challenges experienced with long catheters and provides greater flexibility with regard to the orientation of the RCM with regard to the insertion axis. There is also a need to for an improved catheter system that operates over a smaller footprint and weighs less.

SUMMARY

A medical device comprising a sheath catheter and at least one feed mechanism is disclosed herein. The feed mechanism includes a pair of radially arranged drive wheels opposite one another, each wheel having a wheel rotation axis. The drive wheels cooperate to define a feed axis along which the sheath catheter is advanced and retracted. The feed axis is oriented generally orthogonal to the wheel rotation axes. The feed axis is configured to change the orientation of the sheath catheter when the sheath catheter is disposed within the feed mechanism.

An alternative configuration for a medical apparatus comprises a robotic instrument driver, a sheath splayer and a guide splayer. The sheath splayer and guide splayer are operatively engaged with the robotic instrument driver. The sheath splayer carries the catheter sheath, and the guide splayer carries the sheath catheter. The sheath splayer is defined by a catheter sheath operational axis and the guide splayer is defined by a guide catheter operational axis, wherein the sheath operational axis and guide catheter operational axis are oriented parallel to one another and laterally spaced apart from one another. First and second feed mechanisms are also provided. The first feed mechanism is positioned between the sheath splayer and the guide splayer and configured to orient the guide catheter about 180° from the guide catheter operational axis so as to be coaxial with the catheter sheath operational axis. The second feed mechanism is positioned distally of the sheath splayer and is configured to orient the sheath catheter about 180° from the catheter sheath operational axis so as to be coaxial with a feed axis that is oriented parallel to the catheter sheath operational axis.

A further alternative configuration of a medical device comprises a robotic instrument driver, a sheath splayer and a guide splayer. The sheath splayer and guide splayer are operatively engaged with the robotic instrument driver. The sheath splayer carries the sheath catheter, and the guide splayer carries the guide catheter. The guide splayer is positioned over the sheath splayer in a stacked relationship. The sheath catheter is defined by a sheath catheter operational axis and the guide splayer is defined by a guide catheter operational axis and the sheath operational axis and guide operational axis are oriented parallel to one another and spaced apart from one another. First and second feed mechanisms are also provided. The first feed mechanism is positioned between an entrance of the sheath splayer and an exit of the guide splayer and configured to orient the guide catheter about 180° from the guide catheter operational axis so as to be coaxial with the catheter sheath operational axis. The second feed mechanism is positioned distally of the sheath splayer and is configured to orient the sheath catheter about 180° from the catheter sheath operational axis so as to be coaxial with a feed axis that is oriented parallel to the catheter sheath operational axis.

BRIEF DESCRIPTION OF THE DRAWINGS

While the claims are not limited to a specific illustration, an appreciation of the various aspects is best gained through a discussion of various examples thereof. Referring now to the drawings, exemplary illustrations are shown in detail. Although the drawings represent the illustrations, the drawings are not necessarily to scale and certain features may be exaggerated to better illustrate and explain an innovative aspect of an example. Further, the exemplary illustrations described herein are not intended to be exhaustive or otherwise limiting or restricted to the precise form and configuration shown in the drawings and disclosed in the following detailed description. Exemplary illustrations are described in detail by referring to the drawings as follows:

DETAILED DESCRIPTION OF THE INVENTION

Figure 1:
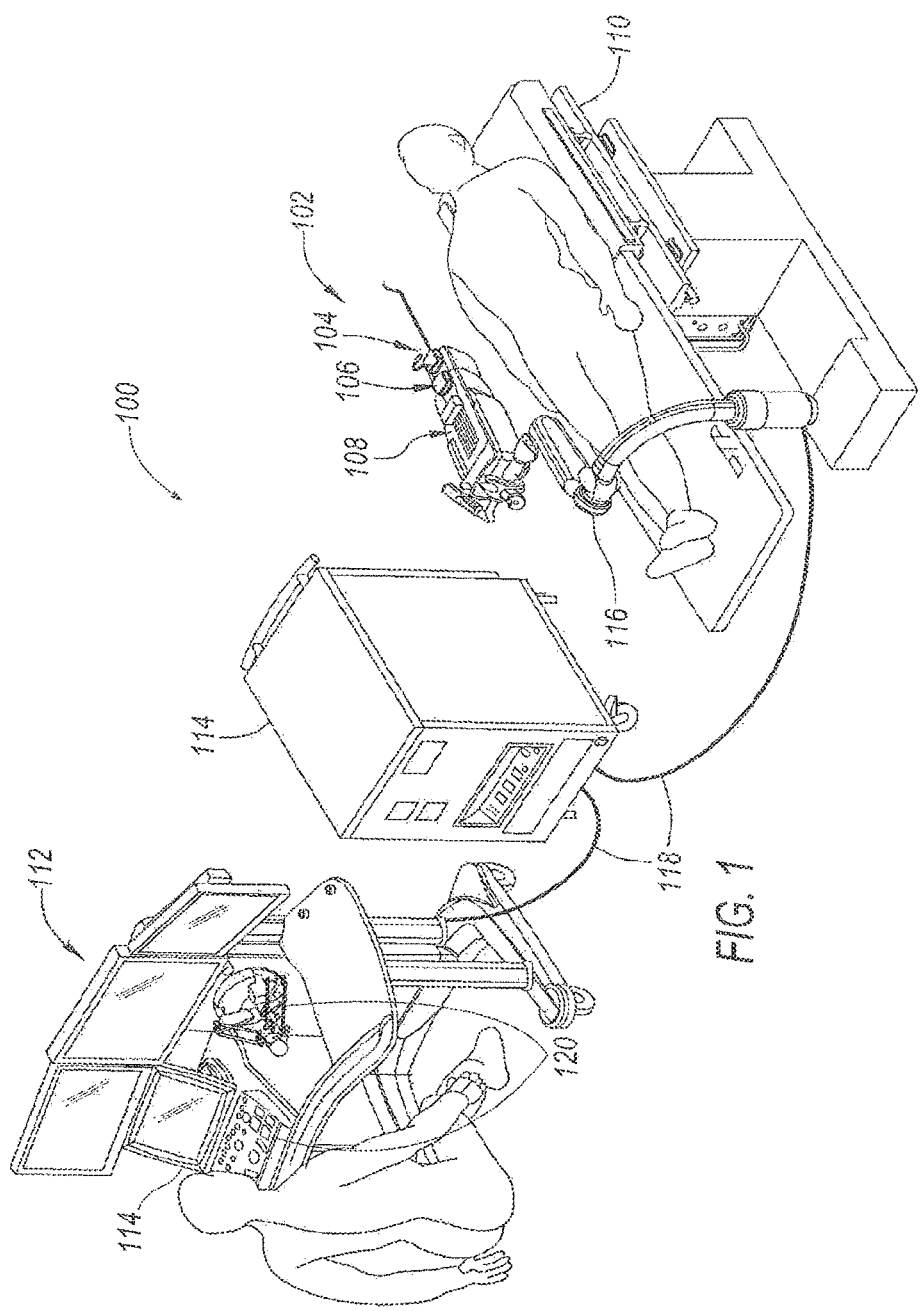
FIG. 1 illustrates an exemplary robotic surgical system.

Referring to FIG. 1, a robotic surgical system 100 is illustrated in which an apparatus, a system, and/or method may be implemented according to various exemplary illustrations. System 100 may include a robotic catheter assembly 102 having a sheath instrument 104 and/or a catheter instrument 106. Catheter assembly 102 is controllable using a robotic instrument driver 108 (generally referred to as "instrument driver"). During use, a patient is positioned on an operating table or surgical bed 110 to which robotic instrument driver 108 is coupled or mounted. In the illustrated example, system 100 includes an operator workstation 112, an electronics rack 114 including a control system, such as a computer (not shown). In some instances, a setup joint mounting brace 116 may be used to support the robotic catheter assembly 102. In certain procedures, a surgeon is seated at operator workstation 112 and can monitor the surgical procedure, patient vitals, and control one or more catheter devices.

Operator workstation 112 may include a computer monitor to display a three dimensional object, such as a catheter displayed within or relative to a three dimensional space, such as a body cavity or organ, e.g., a chamber of a patient's heart. In one example, an operator uses one or more input devices 120 to control the position of a catheter or other elongate instrument. In response to actuation of the input device by a user, the input device can output positioning information for the desired position of the catheter instrument, including the three-dimensional spatial position of the distal end of a steerable catheter. System components, including the operator workstation, electronics rack and the instrument driver, may be coupled together via a plurality of cables or other suitable connectors 118 to provide for data communication, or one or more components may be equipped with wireless communication components to reduce or eliminate cables 118. Communication between components may also be implemented over a network or over the internet. In this manner, a surgeon or other operator may control a surgical instrument while located away from or remotely from radiation sources. Because of the option for wireless or networked operation, the surgeon may even be located remotely from the patient in a different room or building.

Figure 2:
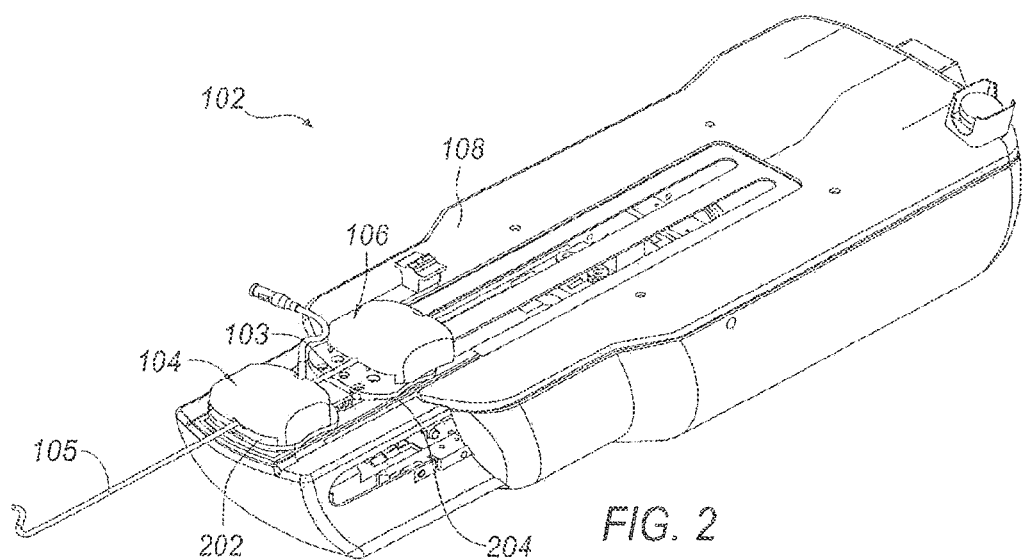
FIG. 2 is an illustration of an exemplary catheter assembly of the surgical system of FIG. 1.

An exemplary instrument driver 108 is illustrated in FIG. 2. The instrument driver 108 may robotically insert/retract a leader catheter 103 relative to a sheath catheter 105. To this end, the proximal ends of sheath catheter 105 and leader catheter 103 are mechanically interfaced to a housing of the instrument driver 108 in such a manner that the sheath and leader catheters 105, 103 may be axially translated relative to each other via operation of motors, thereby effecting insertion or retraction movements of the respective sheath catheter 105 and leader catheter 103. In the illustrated embodiment, the sheath catheter 105 and leader catheter 103 respectively include proximal steering adapters 104, 106 ("splayers") mounted to associated mounting plates 202, 204 on a top portion of the instrument driver 108. The mounting plate 202 is affixed to the distal end of the instrument driver 108, whereas the mounting plate 204 is affixed to a carriage (not shown) within the housing of the instrument driver 108 that can be translated relative to the mounting plate 202 via one or more motors (not shown) within the housing of the instrument driver 1, thereby allowing the splayer 106 to be translated relative to the splayer 104, and thus, the associated leader catheter 103 to be inserted/retracted within the sheath catheter 105. In the illustrated embodiment, each of the splayers 104, 106 can be actuated via motors (not shown) within the housing of the instrument driver 108 to deflect or articulate the distal ends of the respective catheters 103, 104 in any direction.

It is desirable to have the instrument driver 108 positioned close to the patient for a number of reasons, including, for example to facilitate tool removal over the table 110 rather than risk tools falling to the floor. However, the instrument drivers 108 are generally heavy, due to the internal components required to advance and articulate the catheters. Moreover, for procedures where a relatively long stroke of a catheter is used, the instrument driver 108 has a sufficient length to operate the catheter system. Thus, known systems use a setup joint 116 to support the instrument driver 108 close to the patient. The positioning of the instrument driver 108 on the setup joint, however, may lead to other issues, such as blocking intra-operative imaging equipment, such as a C-arm or monitor (not shown).

Further, certain issues are experienced when tool exchanges are required during a procedure. For example, therapeutic tools are inserted into the sheath catheter 105. To accomplish this task, the guide catheter 103 is removed from the sheath catheter 105. A separate guide wire (not shown) is also included, but the tool is advanced over the guide wire for delivery, which takes two people.

To address some of these issues, alternative arrangements of the guide and sheath splayers are proposed herein, which serve to minimize the length and weight of the instrument driver, thereby eliminating the requirement of a SUJ, and even permitting the instrument driver to be mounted directly to a bed rail. Moreover, the exemplary arrangements disclosed herein also provide for positioning of the instrument driver close to the patient, thus permitting the instrument driver to be positioned adjacent an introducer.

Figure 3:
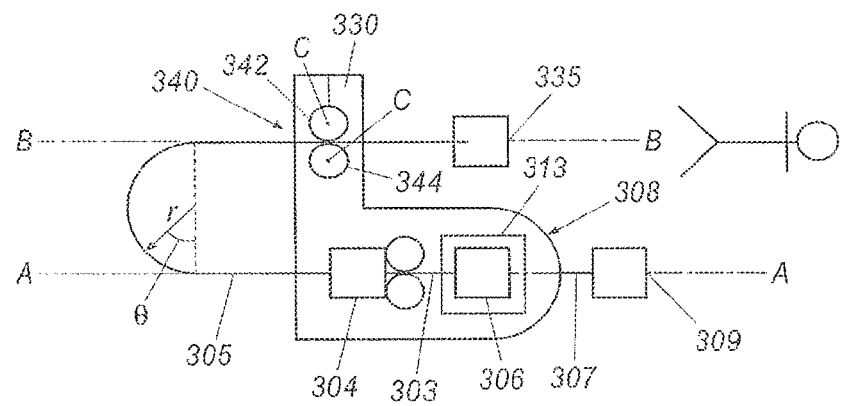
FIG. 3 is a schematic plan view of an embodiment of a robotically controlled medical apparatus.

Referring to FIG. 3, a first exemplary configuration will be described. FIG. 3 illustrates a schematic plan view of an exemplary configuration of an instrument driver 308. A guide splayer 306 and a sheath splayer 304 are operatively mounted to the instrument drive 308. Guide splayer 306 is mounted on a carriage 313 that can translate relative to sheath splayer 304. Operatively connected to the guide splayer 306 is a guide catheter 303, and operatively connected to the sheath splayer 304 is a sheath catheter 305. The carriage 313 inserts the guide catheter 303 into the sheath catheter 305. A guide wire 307 may extend proximally of the guide splayer 306 and further include a guide wire manipulator 309.

In the embodiment illustrated in FIG. 3, sheath splayer 304 and guide splayer 306 are arranged to be generally aligned along a common axis A-A. In this manner, the guide catheter 303 is positioned within the sheath catheter 305, such that the guide catheter 303 and the sheath catheter 305 are arranged in a coaxial manner. Although splayers 304 and 306 are axially aligned, movement of guide catheter 303 and catheter sheath 305 can be controlled and manipulated independently, as will be explained in further detail below. The instrument driver 308 articulates guide and sheath splayer driveshafts by motors positioned in the rear of the instrument driver 308.

In the exemplary arrangement illustrated in FIG. 3, as the sheath catheter 305 exits the sheath splayer 304, the sheath catheter 305 is positioned within a manipulator or feed mechanism 330. This manipulator 330 may be configured to advance, retract or roll sheath catheter 305. It may also be configured to orientate the sheath catheter 305 such that it bends 180 into the feed mechanism 330. More specifically, the mechanism 330 is oriented such that an axis B-B extending through the mechanism 330 is generally parallel with the axis A-A along which the sheath and guide splayers 304, 306 are arranged. The sheath catheter 305 exits the mechanism 330 and can be directed into an introducer 335. This configuration permits a compact design, which can reduce the required length of the instrument driver 308, and also allow for easy draping of the surgical system. Surgical draping is in reference to the use of a curtain, bag, cloth or other acceptable sterile items that may be utilized to separate a sterile area from an unsterile area. It is advantageous to be able to place a surgical drape over items that are difficult to clean or items that need to be in the sterile field but are not sterile. By placing a surgical drape over these items, these items are prevented from coming into contact with sterile items. For example, the instrument driver 308 contains delicate and sensitive parts, so by placing a surgical drape over the instrument driver 308, it will not come into contact with blood or other contaminating materials and may not require cleaning.

In one embodiment, the manipulator mechanism 330 includes two radially oppositely arranged drive wheels 340. The drive wheels 340 may include an idle wheel 342 and an active wheel 344. The drive wheels 340 are each configured to rotate about an axes C-C that are orthogonal to the feed mechanism axis B-B. In one exemplary arrangement, the feed mechanism 330 may be fixedly connected to the instrument driver 308, along a side surface of the instrument driver 308. This configuration permits the feed mechanism to be placed next to the axis A-A so as to minimize wasted catheter length. As the drive wheels 340 are rotated in a first direction, the feed mechanism 330 serves to propel the sheath catheter 305, the guide catheter 303 inserted therein, and the guide wire 307 toward the patient. As the drive wheels 340 are rotated in a second direction, the catheter assembly is moved away from the patient. A similar manipulator mechanism (not shown) disposed within the instrument driver 308 proximal of the sheath splayer 304 serves to propel guide catheter 303. This manipulation may also involve insertion retraction or roll of the guide catheter relative to the sheath. In addition, a similar manipulator mechanism (not shown) disposed within the instrument driver 308 proximal of the leader splayer 306, or disposed proximal of instrument driver 308 (as shown) serves to propel the guide wire 307. It should be understood that sheath catheter 305, guide catheter 303 and guide wire 307 may all be manipulated independently from each other. Manipulation may involve insertion, retraction and roll for all 3 manipulators but preferred embodiments involve just insertion and retract for the sheath and guide manipulators and insertion, retraction and roll for the guidewire manipulator. It should be understood that while drive wheels are shown for the sheath manipulator 330 and a gripping pad 309 is shown for the guidewire manipulator, any active drive or manipulation device such as rotating pads, grippers, rollers, chucks etc. may be used in all cases In one alternative embodiment, the manipulator 330 may be configured to pitch with respect to the drive wheels axes C-C, while the sheath splayer 304 and guide splayer 306 remain generally level with respect to the table 110. With this configuration, the opposing drive wheels 340 may be configured to selectively adjust an insertion angle of the catheter assembly as the catheter sheath 305 passes through the manipulator 340.

Figure 4A:
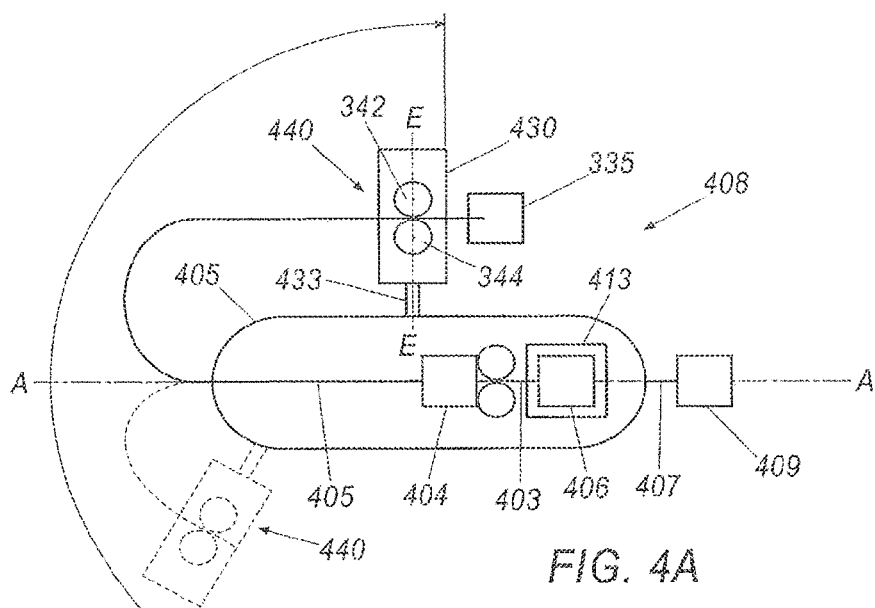
FIG. 4A illustrates a schematic plan view of a robotically controlled medical apparatus having a selectively positionable feed mechanism.

An alternative configuration of an instrument driver 408 is illustrated in FIG. 4A. Instrument driver 408 is substantially similar to the instrument driver 308 of FIG. 3 and may include corresponding features identified with reference numerals in the 400 series. More specifically, the instrument driver 408 includes a guide splayer 406 and a sheath splayer 404 operatively connected thereto. A guide catheter 403 is connected to the guide splayer 406 and the catheter sheath 405 is operatively connected to the sheath splayer 404. The guide splayer 406 is installed on a slidable carriage 413 that translates relative to sheath splayer 404. A guide catheter manipulator (not shown) is placed proximal to the sheath splayer to manipulate the guide catheter A guide wire 407 may extend proximally from the guide splayer 406 and further include a guide wire manipulator 409.

Figure 4B:
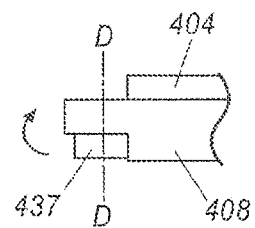
FIG. 4B is a partial elevational view of a distal end of the robotically controlled medical apparatus of FIG. 4A.

In the exemplary arrangement illustrated in FIG. 4A, as the sheath catheter 405 exits the sheath splayer 404, the sheath catheter 405 is positioned within a manipulator 430. However, in this embodiment, the manipulator 430 is connected to the instrument driver 408 such that the manipulator 430 may be selectively rotated about axis A-A along an arc. In one exemplary arrangement, the feed mechanism 430 may be mounted to a shaft 433 that is secured to a wheel 437 (shown in FIG. 4B) mounted for rotation about an axis D-D. With this configuration, feed mechanism 430 may be selectively repositioned from one side of the instrument driver 408 to the other, as illustrated by feed mechanism 440 displayed in phantom in FIG. 4A. The selective positioning of feed mechanism 440 allows for repositioning of the instrument driver 408 during a procedure to clear the surgical site so as to allow for fluoroscopy imaging. The selective positioning of feed mechanism 440 also allows for selective placement of the instrument driver 408 on either side of patient.

In another exemplary arrangement, sheath splayer 404 may rotate about an axis D-D to minimize wasted length on the sheath catheter. For example, as sheath 405 is inserted into the patient, via manipulator 409, the sheath splayer 404 may be configured to rotate toward the manipulator to minimize the length of catheter outside of the patient.

In one exemplary arrangement, the manipulator 430 may be configured to pitch with respect to an axis E-E that extends through the shaft 433, while the sheath splayer 404 and guide splayer 406 remain generally level with respect to the table 110. With this configuration, the opposing drive wheels 440 may be configured to selectively adjust an insertion angle of the catheter assembly as the catheter sheath 405 passes through the mechanism 440.

Figure 5:
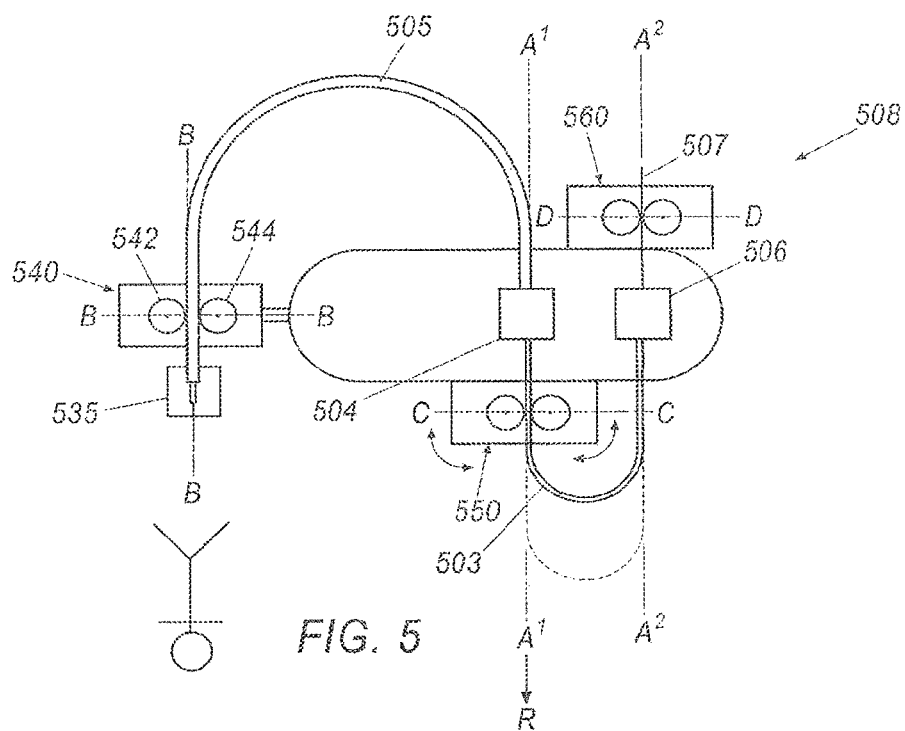
FIG. 5 illustrates a schematic plan view of an alternative configuration for a robotically controlled medical apparatus having operational axes of catheter splayers and guide splayers oriented parallel to one another.

An alternative configuration of an instrument driver 508 is illustrated in FIG. 5. Instrument driver 508 has similar elements to the instrument driver 408 of FIG. 4 and may include corresponding features identified with reference numerals in the 500 series. More specifically, the instrument driver 508 includes guide splayer 506 and a sheath splayer 504 operatively connected thereto. A guide catheter 503 is connected to the guide splayer 506 and the catheter sheath 505 is operatively connected to the sheath splayer 504. A guide wire 507 may extend proximally of the guide splayer 506 and further include a guide wire manipulator 560.

The configuration of the instrument driver 508 in FIG. 5 differs from the arrangements shown in FIGS. 3-4 in that the guide splayer 506 and the sheath splayer 504 are arranged parallel to one another, as opposed to in-line with one another. In addition, the guide splayer 506 does not translate relative to sheath splayer 504. The guide catheter 503 bends 180° and feeds into the sheath splayer 504 by a guide manipulator mechanism 550 that is disposed at the entrance of the sheath splayer 504. The sheath catheter 505 also bends 180°, but in the opposite direction than the guide catheter 503, such that the catheter assembly is arranged in a general "S-shape". The sheath catheter 505 feeds into an introducer 535 by a sheath manipulator mechanism 540.

The guide feed mechanism 550 is configured to orient the guide catheter 503 such that it bends 180° into the guide mechanism 550. More specifically, the mechanism 550 is oriented such that an axis extending through the guide mechanism 550 is generally coaxial with an axis A'-A' along which the sheath splayer 504 is positioned. The sheath mechanism 540 is configured to orient the sheath catheter 505 such that it bends 180° into the sheath mechanism 540. More specifically, the sheath mechanism 540 is oriented such that an axis B-B extending through the sheath mechanism 540 is generally parallel to the axis A'-A' along which the sheath splayer 504 is positioned at the start of a procedure. The sheath splayer 504 may be configured to rotate towards manipulator 540 as the sheath 505 is inserted through introducer 535 and the available sheath length outside the patient gets shorter.

A guidewire manipulator mechanism 560 is positioned adjacent an entrance to the guide splayer 506. The guidewire mechanism 560 is oriented such that an axis extending through the guide feed mechanism 560 is generally coaxial with an axis A2-A2 along which the guide splayer 506 is positioned. The guidewire manipulator 560 may also be configured to insert, retract and roll a guidewire. It should be understood that the feed roller embodiment of the guidewire manipulator 560 shown here and the gripper embodiment 409 shown above are representative embodiments of active drive manipulators. Any of these manipulation mechanisms may be used in any of the configurations.

The orientation of the sheath and guide splayers 504, 506 eliminates a linear insertion axis of the catheter sheath 505 and guide catheter 503, thereby reducing the size of the instrument driver 508. Reducing the size of the instrument driver 508 lends itself to a simple surgical drape of the catheter system.

The configuration of a catheter system with three different manipulator mechanisms 540, 550, 560 also allows the guide wire 507, guide catheter 503 and/or the sheath catheter 505 to be propelled or held in place individually. More specifically, the sheath mechanism 540 may be configured to insert, retract or roll the sheath catheter 505. The guide mechanism 550 inserts, retracts or rolls the guide catheter 503 and the guide wire mechanism 560 inserts, retracts or rolls guidewire 507. Thus, the combination of the three feed mechanisms 540, 550, and 560 allows the guide wire 507, sheath catheter 505, and/or guide catheter 503 (as shown in FIG. 5) to be propelled or held in place individually, altering the shape of the catheter system relative to a tip of the guide wire 507.

In such fashion and in one example, a robotic instrument driver for elongate members 508 includes a first elongate member 505, and at least one manipulator mechanism 540 configured to manipulate the first elongate member 505, and at least one articulating drive 504 configured to articulate the first elongate member 505, positionable on a bed 110 and beside a patient access site, wherein the manipulator 540 and articulating drive 504 are positioned relative to each other a distance less than the insertable length of the first elongate member, stationary in position. That is, a distance between manipulator 540 (and particularly between wheels 542, 544) and articulating drive 504 is less than a length of the first elongate member 505 that passes between them—i.e., the insertable length.

In one exemplary configuration, the sheath mechanism 540 may be configured to pitch with respect to an axis B-B that is generally transverse to the feed axis B-B, while the sheath splayer 504 and guide splayer 506 remain generally level with respect to the table 110. With this configuration, opposing drive wheels 542, 544 may be configured to selectively adjust an insertion angle of the catheter assembly as the catheter sheath 505 passes through the catheter feed mechanism 540.

The configuration in FIG. 5 also provides for ease of tool exchange during an intra-operative procedure. In fact, tool exchange can be performed by a single individual with the configuration set forth in FIG. 5, allowing for improved workflow. The tool exchange operation will be explained in further detail below.

Figure 6:
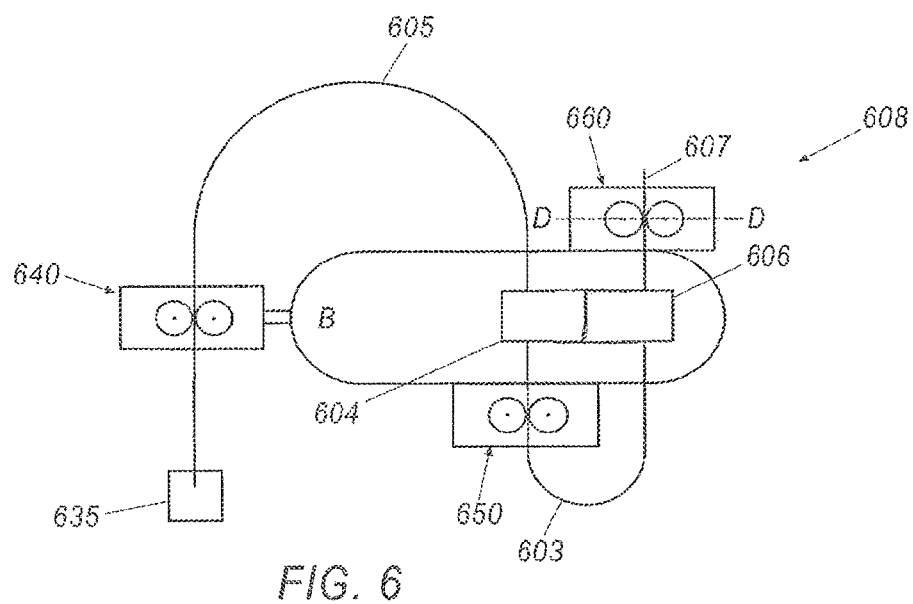
FIG. 6 illustrates a schematic plan view of an alternative configuration for a robotically controlled medical apparatus of FIG. 5, wherein the catheter splayer and guide splayer are configured as a combined unit.

Referring to FIG. 6, another alternative configuration for an exemplary instrument driver 608 is illustrated. Instrument driver 608 is substantially similar to the instrument driver 508 of FIG. 5 and may include corresponding features identified with reference numerals in the 600 series. However, the instrument driver 608 includes a combined sheath splayer 604/guide splayer 606, which are oriented in a parallel manner creating an S-shape catheter configuration similar to that which is shown and discussed above in connection with FIG. 5.

Figure 7:
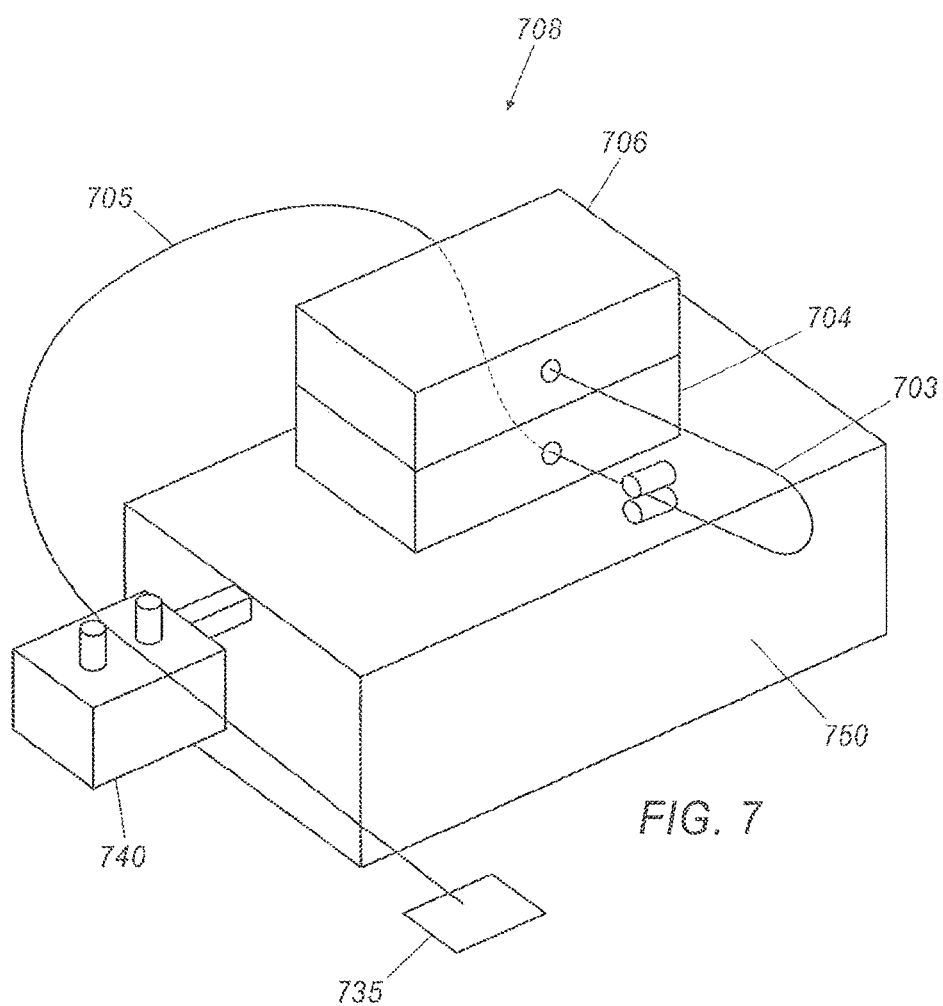
FIG. 7 illustrates a schematic perspective view of an alternative configuration for an exemplary robotically controlled medical apparatus including a guide splayer and sheath splayer assembled together in a stacked relationship.

Referring to FIG. 7, a further exemplary arrangement of for an instrument driver 708 will now be described. Instrument driver 708 is similar to the configuration of instrument driver 608 of FIG. 6 and may include corresponding features identified with reference numerals in the 700 series. The instrument driver 708 has the guide splayer 706 and sheath splayer 704 stacked on top of one another. Stacking the guide splayer 706 on top of the sheath splayer 704 may further reduce the size of the instrument driver 708 as compared to other configurations. The guider catheter 703, as it exits the guide splayer 706, bends approximately 180° to where it is received by the sheath manipulator mechanism 750 and directed into the sheath splayer 704, orienting the guide catheter 703 in a generally vertical C-shape guide. The catheter sheath 705 exits the sheath splayer 704 and bends approximately 180° to where it is received by the sheath mechanism 740, orienting the catheter sheath 705 in a generally horizontal C-shape.

Figure 8A:
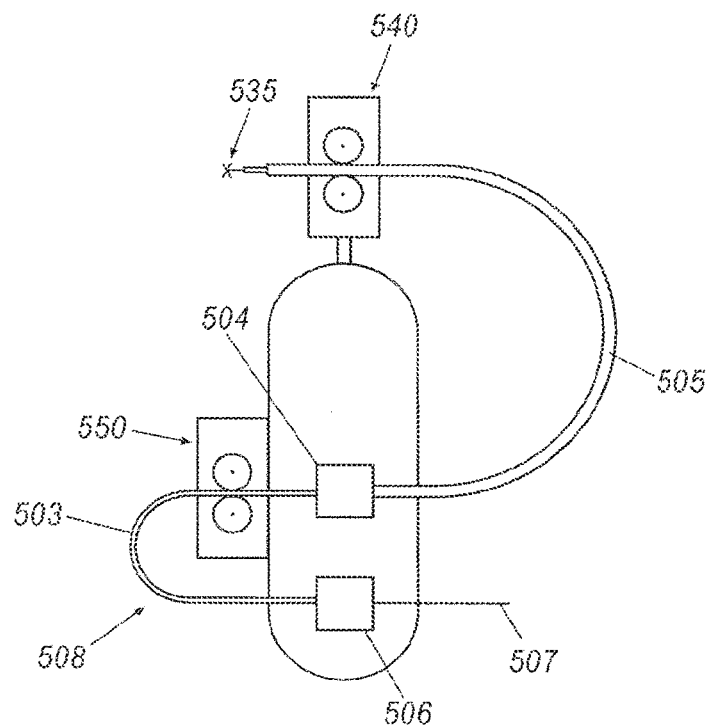
FIG. 8A-8C illustrates an exemplary process for removing a tool from the robotically controlled medical apparatus of FIG. 5.
Figure 8B:
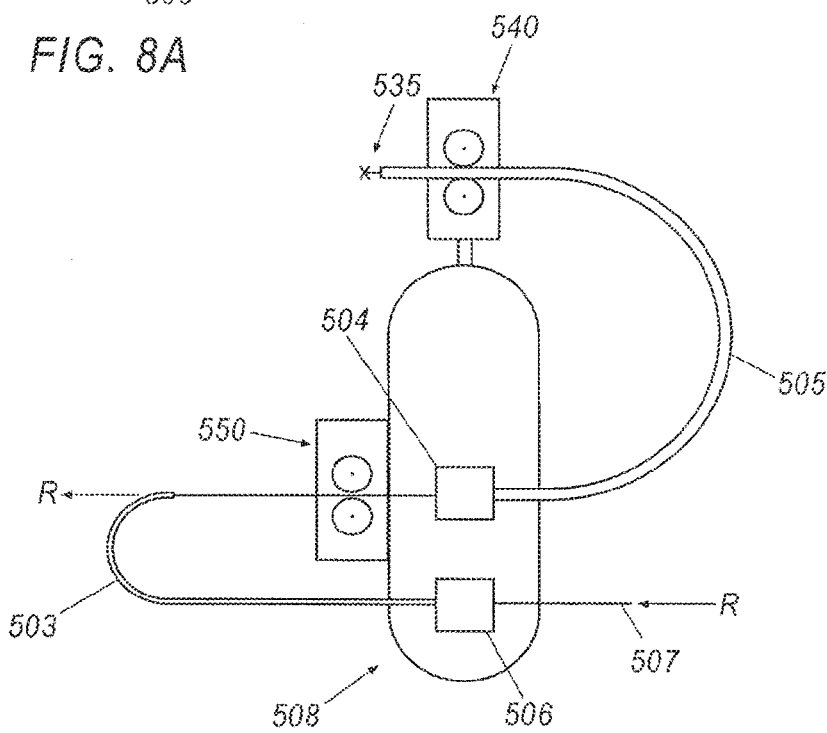
Figure 8C:
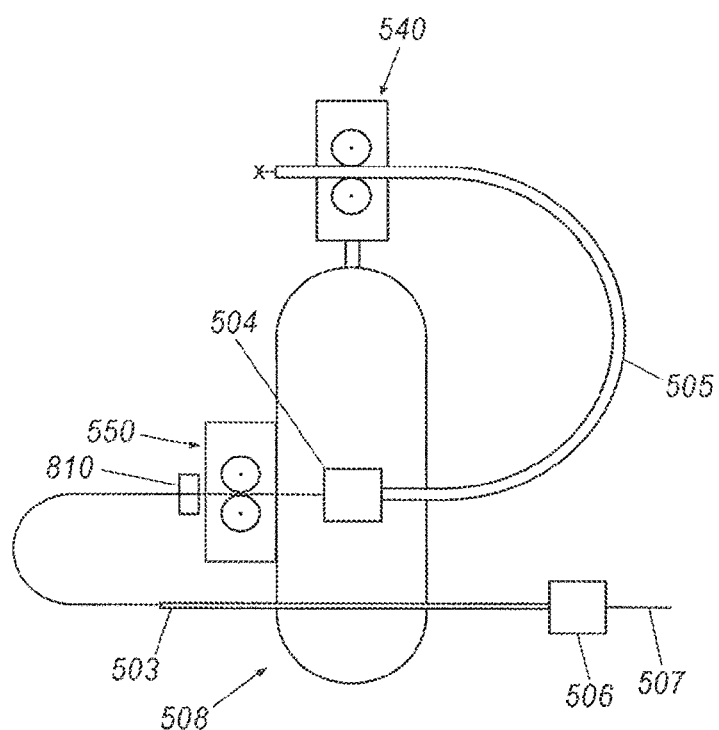

Referring to FIG. 8A-8C, an exemplary process for removing guide 503 or any other tool robotically or manually from the sheath catheter 505 will now be explained. For ease of description, the configuration of the instrument driver 508 will be used to explain the tool exchange process.

FIGS. 8A-C illustrate the instrument driver 508 including guide or tool 503 connected to the guide splayer 506, sheath splayer 504, catheter manipulator mechanism 540 and tool (guide) manipulator mechanism 550 arranged so as to configure the catheter system in a generally S-shape configuration. To remove the guide or tool 503, the tool 503 and the guide wire 507 are both pulled in unison in direction R. In other words, the guide wire is inserted into the tool or guide at the same rate as the tool or guide is retracted from the sheath. This action will cause the guide wire 507 to be pulled through the guide splayer 506, as indicated by the phantom lines. This results in maintaining the tip of the guidewire in a fixed position relative to the sheath or relative to the patient. Once the guide catheter 503 is free from the sheath splayer 504, clamping or pinching 810 of the tool (guide) feed mechanism 550 may be applied to the wire 507 at the rear of the sheath splayer 504 to hold the tip of the wire 507 at the distal end thereof (located in the introducer 535 and thus not visible). The guide or tool may then be slid along the guide wire 507, until the guide or tool 503 is free from the guide wire 507, thereby removing the guide or tool 503 from the instrument driver 508. Once the guide or tool 503 is removed from the guide wire 507, a new tool may be installed over the guide wire 507. A similar but opposite sequence of moves enables the new tool to be loaded robotically into the sheath 505. This time, the guidewire 507 is retracted through manipulator 560 at the same rate as the new tool is inserted through manipulator 550 resulting in the distal tip of the wire not moving relative to the patient. The ability to change tools may allow the user to perform multiple procedures without having to remove the catheter sheath 505 from the patient between procedures. For example, a patient may require multiple therapeutic devices to be delivered at the same location. The ability to maintain the tip of the guide wire 507 at a deployed location in the body after a first tool is delivered allows the user to switch the tool 503 and insert the second therapeutic device without removing the entire catheter. Using a robotic system to exchange tools enable the tool exchange procedure to be carried out without image guidance such as fluoroscopy. With a manual procedure, the doctor would need to retract the guide with one hand at the same rate as he is inserting the wire with the other hand to ensure the wire tip stays in a fixed position. It is not possible for a human to coordinate movement of both hands reliably with long catheters and so fluoroscopic guidance is used to ensure the wire is not moving. Fluoroscopic imaging exposes doctors and staff to significant radiation. A robotic system with active drive manipulators as described here addresses this issue With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

What is claimed is:

1. A robotic system, comprising:
a medical instrument comprising an elongate member configured for insertion into a patient;
a splayer coupled to a first portion of the elongate member, the splayer configured to articulate a distal end of the elongate member; and
a manipulator comprising drive wheels configured to axially translate the elongate member along a feed axis along which the elongate member is insertable into and retractable from the patient;
wherein the splayer and the manipulator are oriented such that the elongate member bends and follows a non-linear path between the splayer and the manipulator.

2. The robotic system of claim 1, wherein the manipulator and the splayer are repositionable relative to each other.

3. The robotic system of claim 2, wherein the splayer is configured to be rotated toward the manipulator.

4. The robotic system of claim 1, further comprising an instrument driver operatively coupled to the medical instrument through a mechanical interface on the splayer.

5. The robotic system of claim 1, wherein the manipulator is configured to hold and propel the elongate member.

6. The robotic system of claim 1, wherein the manipulator is configured to roll the elongate member.

7. The robotic system of claim 1, wherein the elongate member bends at least 180 degrees.

8. The robotic system of claim 1, wherein the first portion of the elongate member and a second portion of the elongate member are substantially parallel to each other.

9. The robotic system of claim 1, wherein the elongate member is further coupled to an introducer.

10. The robotic system of claim 1, wherein a distance between the splayer and the manipulator is less than a length of the elongate member between the splayer and the manipulator.

11. The robotic system of claim 1, wherein the splayer is positioned along a first axis, wherein the first axis and the feed axis are non-coaxial.

12. A method comprising:
articulating a distal end of an elongate member of a medical instrument with a splayer; and
axially translating the elongate member along a feed axis to insert and retract the elongate member within a patient with drive wheels of a manipulator;
wherein the splayer and the manipulator are oriented such that the elongate member bends and follows a non-linear path between the splayer and the manipulator.

13. The method of claim 12, further comprising repositioning the manipulator relative to the splayer.

14. The method of claim 13, further comprising rotating the splayer toward the manipulator.

15. The method of claim 12, further comprising articulating the distal end of the elongate member in response to actuation from an instrument driver operatively coupled to the medical instrument through a mechanical interface on the splayer.

16. The method of claim 12, further comprising advancing, retracting, or rolling the elongate member in response to actuation from an instrument driver operatively coupled to the medical instrument through a mechanical interface on the splayer.

17. The method of claim 12, further comprising holding and propelling the elongate member with a drive mechanism of the manipulator.

18. The method of claim 12, further comprising feeding the elongate member into an introducer with the manipulator.

19. The method of claim 12, further comprising positioning the splayer and the manipulator at a distance less than a length of the elongate member between the splayer and the manipulator.

20. The method of claim 12, further comprising adjusting an insertion angle of the elongate member with the manipulator.

* * * * *